(12) United States Patent
El-Khouri

(10) Patent No.: US 11,179,313 B2
(45) Date of Patent: *Nov. 23, 2021

(54) COSMETIC COMPOSITIONS COMPRISING SILICONE AND HYDROCARBON CAPABLE OF FORMING A MULTILAYER STRUCTURE AFTER APPLICATION TO A KERATINOUS MATERIAL

(71) Applicant: L'OREAL, Paris (FR)

(72) Inventor: Rita El-Khouri, Morristown, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/253,071

(22) Filed: Aug. 31, 2016

(65) Prior Publication Data

US 2017/0281521 A1    Oct. 5, 2017

Related U.S. Application Data

(63) Continuation-in-part of application No. 15/144,698, filed on May 2, 2016, now Pat. No. 10,675,226, and a continuation-in-part of application No. 15/144,622, filed on May 2, 2016, now Pat. No. 10,772,806, and a continuation-in-part of application No. 15/144,716, filed on May 2, 2016, now Pat. No. 10,744,074.

(60) Provisional application No. 62/316,309, filed on Mar. 31, 2016.

(51) Int. Cl.
| | |
|---|---|
| A61K 8/892 | (2006.01) |
| A61Q 1/04 | (2006.01) |
| A61Q 1/02 | (2006.01) |
| A61K 8/31 | (2006.01) |
| A61K 8/891 | (2006.01) |
| A61K 8/60 | (2006.01) |

(52) U.S. Cl.
CPC ........... *A61K 8/892* (2013.01); *A61K 8/31* (2013.01); *A61K 8/60* (2013.01); *A61K 8/891* (2013.01); *A61Q 1/02* (2013.01); *A61Q 1/04* (2013.01); *A61K 2800/87* (2013.01); *A61K 2800/88* (2013.01)

(58) Field of Classification Search
CPC ........... A61K 8/892; A61K 2800/87; A61K 2800/43; A61K 2800/59; A61K 2800/594; A61Q 1/04; A61Q 1/02; A61Q 8/31; A61Q 8/89; A61Q 8/60
See application file for complete search history.

(56) References Cited

U.S. PATENT DOCUMENTS

| | | |
|---|---|---|
| 4,767,741 A | 8/1988 | Komor et al. |
| 5,849,316 A | 12/1998 | Mullul et al. |
| 5,882,635 A | 3/1999 | Ramin et al. |
| 5,985,297 A | 11/1999 | Mullul et al. |
| 6,019,962 A | 2/2000 | Rabe et al. |
| 6,071,503 A | 6/2000 | Drechsler et al. |
| 6,340,466 B1 | 1/2002 | Drechsler et al. |
| 6,406,683 B1 | 6/2002 | Drechsler et al. |
| 6,482,398 B1 | 11/2002 | Rabe et al. |
| 6,620,417 B1 | 9/2003 | Jose et al. |
| 6,811,770 B2 | 11/2004 | Ferrari et al. |
| 7,785,574 B2* | 8/2010 | Bobka ............ A61K 8/31 424/401 |
| 8,277,791 B2 | 10/2012 | Zheng et al. |
| 9,205,039 B2* | 12/2015 | Brown ............ A61K 8/042 |
| 2001/0031269 A1 | 10/2001 | Arnaud |
| 2003/0068344 A1 | 4/2003 | Ferrari et al. |
| 2004/0141933 A1 | 7/2004 | Luo et al. |
| 2005/0089498 A1 | 4/2005 | Patil et al. |
| 2005/0186166 A1 | 8/2005 | Patil et al. |
| 2005/0201961 A1* | 9/2005 | Lu ............ A61K 8/585 424/63 |
| 2005/0226832 A1 | 10/2005 | Bobka et al. |
| 2005/0244355 A1 | 11/2005 | Sabino et al. |
| 2005/0249758 A1 | 11/2005 | Di Puccio Pagano |
| 2006/0292096 A1 | 12/2006 | Yu |
| 2007/0093619 A1 | 4/2007 | Bui et al. |
| 2007/0142521 A1 | 6/2007 | Brahms et al. |
| 2008/0305056 A1* | 12/2008 | Jenni ............ A61K 8/416 424/59 |
| 2008/0305068 A1 | 12/2008 | Zheng et al. |
| 2008/0317686 A1* | 12/2008 | Mateu ............ A61K 8/0212 424/59 |

(Continued)

FOREIGN PATENT DOCUMENTS

| | | |
|---|---|---|
| EP | 1 518 535 A1 | 3/2005 |
| EP | 2 298 273 A1 | 3/2011 |

(Continued)

OTHER PUBLICATIONS

Patel et al. "Surface and Bulk Phase Separation in Block Copolymers and their blends. Polysulfone/polysiloxane," in Macromolecules, vol. 21, No. 9, 1988, pp. 2689-2696.*

(Continued)

*Primary Examiner* — Blessing M Fubara
(74) *Attorney, Agent, or Firm* — Oblon, McClelland, Maier & Neustadt, L.L.P.

(57) ABSTRACT

Cosmetic compositions capable of forming a multilayer structure after application to a keratinous material are provided, as well as methods of applying such compositions to a keratinous material. Certain cosmetic compositions comprises at least two immiscible components: Component A which comprises about 0.01% to 60% by weight with respect to the total weight of the composition of at least one hydrocarbon-containing film forming agent having at least one glass transition temperature which is lower than normal human body temperature; and Component B which comprises about 0.01% to 90% by weight with respect to the total weight of the composition of one or more silicone compounds in amounts sufficient to achieve a viscosity of about 1,000 cSt to 10,000,000 cST, wherein the weight ratio of hydrocarbon-containing film forming agent(s) in Component A to silicone compound(s) in Component B is from about 1:50 to 50:1.

14 Claims, No Drawings

(56) References Cited

U.S. PATENT DOCUMENTS

| | | |
|---|---|---|
| 2011/0147259 A1 | 6/2011 | Binder et al. |
| 2012/0276034 A1 | 11/2012 | Zheng et al. |
| 2012/0308500 A1 | 12/2012 | Hart |
| 2013/0164229 A1* | 6/2013 | Mendoza ............ A61K 8/31 424/59 |
| 2014/0154196 A1* | 6/2014 | Cavazzuti ............ A61K 8/37 424/64 |
| 2014/0154199 A1 | 6/2014 | Dussaud et al. |
| 2015/0366779 A1 | 12/2015 | Bui et al. |
| 2015/0366780 A1 | 12/2015 | Bui et al. |
| 2015/0366782 A1 | 12/2015 | Bui et al. |
| 2016/0228349 A1 | 8/2016 | Dussaud et al. |
| 2017/0135946 A1 | 5/2017 | Novack et al. |

FOREIGN PATENT DOCUMENTS

| | | |
|---|---|---|
| EP | 2 589 372 | 5/2013 |
| EP | 2 716 277 A1 | 4/2014 |
| JP | 2015-520118 A | 7/2015 |
| WO | WO 2014-095821 A1 | 6/2014 |
| WO | WO 2015/193413 A1 | 12/2015 |

OTHER PUBLICATIONS

U.S. Appl. No. 15/144,622, filed May 2, 2016, 2017-0281478-A1, Rita El-Khouri.

U.S. Appl. No. 15/144,698, filed May 2, 2016, 2017-0281518-A1, Rita El-Khouri.

U.S. Appl. No. 15/144,716, filed May 2, 2016, 2017-0281520-A1, Rita El-Khouri.

U.S. Appl. No. 15/253,114, filed Aug. 31, 2016, 2017-0281519-A1, Rita El-Khouri.

U.S. Appl. No. 15/445,634, filed Feb. 28, 2017, Rita Jaky El-Khouri.

U.S. Appl. No. 15/445,684, filed Feb. 28, 2017, Rita Jaky El-Khouri.

International Search Report and Written Opinion dated Jul. 11, 2017, in PCT/US2017/025370.

The International Search Report and Written Opinion of the International Searching Authority dated Jul. 11, 2017 in PCT/US2017/025376 filed Mar. 31, 2017, 14 pages.

"Xiameter(R) PMX-200 Silicone Fluid 30,000 CS" XIAMETER® from Dow Corning, Safety Data Sheet, Version 3.0, Revision Date: Sep. 13, 2017, pp. 1-12.

"XIAMETER® PMX-200 Silicone Fluid, 5,000-60,000 cSt" XIAMETER® from Dow Corning, Feb. 18, 2015, 3 Pages.

"Mega Last Liquid Lipstick, Liquid Lipstick: Improved Color Intensity, Non-transfer" Formulation 01451, Dow Corning®, Formulation Information, Color Cosmetics, 2010, 2 Pages.

Alex C. M. Kuo, "Poly(dimethylsiloxane)" Polymer Data Handbook, Copyright © by Oxford University Press, Inc., 1999, pp. 411-435.

"Introduction to Silicone Fluids" Clearco, Aug. 7, 2006, 4 Pages.

Triethoxy Caprylylsilane Treatment—11S KOBO, Jul. 14, 2017, 2 pages.

U.S. Appl. No. 15/857,045, filed Dec. 28, 2017, Rita Jaky El-Khouri.

U.S. Appl. No. 15/719,788, filed Sep. 29, 2017, Rita Jaky El-Khouri.

U.S. Appl. No. 15/720,341, filed Sep. 29, 2017, Rita Jaky El-Khouri.

U.S. Appl. No. 15/857,066, filed Dec. 28, 2017, Rita Jaky El-Khouri.

European Search Report in corresponding application No. 17776774.6 dated Nov. 25, 2019.

Sagitani, "Making Homogeneous and Fine Droplet O/W Emulsions Using Nonionic Surfactants", JAOCS, pp. 738-743, 1981.

Japanese Office Action dated Jun. 2, 2020 in Patent Application No. 2018-551342, 3 pages.

Extended European Search Report and Written Opinion dated Mar. 23, 2020 in 17776774.6, 23 pages.

"Aqua Laque Lipstick" Database GNPD [Online] Mintel, Retrieved from www.gnpd.com, Database Accession No. 3534433, XP055675012, Oct. 27, 2015, 4 pages.

"Velvet Matte Lip Pencil" Database GNPD [Online] Mintel, Retrieved from www.gnpd.com, Database Accession No. 2097358, XP055675014, Jun. 13, 2013, 2 pages (Abstract).

* cited by examiner

COSMETIC COMPOSITIONS COMPRISING SILICONE AND HYDROCARBON CAPABLE OF FORMING A MULTILAYER STRUCTURE AFTER APPLICATION TO A KERATINOUS MATERIAL

CROSS-REFERENCE TO RELATED APPLICATIONS

This application claims the benefit of U.S. Non-provisional application Ser. Nos. 15/144,622, 15/144,698 and 15/144,716, each of which was filed May 2, 2016, and each of which claim priority to U.S. Provisional Application Ser. No. 62/316,309, filed Mar. 31, 2016, the entire contents of each of which is hereby incorporated by reference.

FIELD OF THE INVENTION

The present invention relates to cosmetic compositions capable of forming a multilayer structure after application to a keratinous material. Such compositions allow for benefits associated with multilayer cosmetic products without having to engage in a multi-step application process.

DISCUSSION OF THE BACKGROUND

Many cosmetic compositions, including pigmented cosmetics such as foundations and lipsticks, have been formulated in an attempt to possess long wearing properties upon application. Unfortunately, many of these compositions do not generally possess both good long-wear/transfer-resistance properties as well as good application properties, good comfort properties and/or good appearance properties (for example, shine, gloss or matte properties).

For example, with respect to lip products, commercial products containing silicon resins such as MQ resins are known. Such products are known to provide good long wear properties and/or transfer-resistance. However, such products possess poor application properties, poor feel upon application (for example, feel rough) and poor shine or gloss properties owing to the film formed by the MQ resin (for example, a matte appearance). Therefore, a second composition (topcoat) is separately applied to such products to improve poor properties of the compositions to make the products acceptable to consumers. Furthermore, the topcoat composition must be reapplied continually so that the product remains acceptable to consumers, meaning that the products are effectively not "long-wearing" as they require constant maintenance and reapplication.

Also, with respect to foundations, such products can provide good long wear properties and/or transfer-resistance. However, such long-wearing/transfer-resistant products can possess poor application and/or feel upon properties application, as well as poor matte properties.

Thus, there remains a need for improved "single step" cosmetic compositions having improved cosmetic properties, particularly good wear, feel, shine, gloss and/or matte characteristics upon application.

SUMMARY OF THE INVENTION

The present invention relates to cosmetic compositions capable of forming a multilayer structure after application to a keratinous material.

Accordingly, one aspect of the present invention is a care and/or makeup and/or treatment composition for keratinous materials which has good cosmetic properties such as, for example, good adhesion, transfer-resistance, feel, gloss (or shine), and/or matte upon application, and which can be applied to a keratinous material without having to engage in a multi-step application process.

One aspect of the invention pertains to a cosmetic composition capable of forming a multilayer structure after application to a keratinous material. In one or more embodiments, the cosmetic composition comprises at least two immiscible components: Component A and Component B. In some embodiments, Component A comprises about 0.01% to 60% by weight with respect to the total weight of the composition of at least one hydrocarbon-containing film forming agent having at least one glass transition temperature which is lower than normal human body temperature. In one or more embodiments, Component B comprises about 0.01% to 90% by weight with respect to the total weight of the composition of one or more silicone compounds in amounts sufficient to achieve a viscosity of about 1,000 cSt to 10,000,000 cSt. The weight ratio of hydrocarbon-containing film forming agent(s) in Component A to silicone compound(s) in Component B may be from about 1:50 to 50:1.

In one or more embodiments, the cosmetic composition comprises at least two immiscible components prior to application. In some embodiments, the cosmetic composition comprises an aqueous phase. In one or more embodiments, Component A comprises at least one silicone-containing film forming agent having at least one glass transition temperature lower than 60° C. In some embodiments, the cosmetic composition comprises at least one coloring agent. In one or more embodiments, Component B comprises at least polymer having at least one glass transition temperature lower than 60° C. In some embodiments, Component B is self-leveling such that it imparts shine to the cosmetic composition after application to a keratinous material. In one or more embodiments, the silicone compound comprises at least one silicone gum. In some embodiments, the silicone compound comprises at least one silicone fluid. In one or more embodiments, Component A and Component B have a density difference of 0.001-1 kg/m³. In some embodiments, Component A and Component B have a density difference of 0.01-0.6 kg/m³. In one or more embodiments, Component B comprises at least one polymer having a viscosity of about 1000 cSt to about 1,000,000 cSt. In some embodiments, the silicone compound comprises at least one polymer selected from the group consisting of a silicone gum, a silicone fluid, and mixtures thereof. In one or more embodiments, at least one hydrocarbon-containing film forming agent comprises at least one film forming agent selected from the group consisting of polysaccharides, high viscosity esters, polybutenes, polyisobutenes, polyhydrogenated butenes acrylic polymers, acrylate copolymers, vinyl pyrrolidone (VP) containing homopolymers and copolymers, polyurethanes, polyolefins and mixtures thereof. In some embodiments, Component A comprises at least one polymer having a critical molecular weight of entanglement ($M_c$) such that $M_c < wMw$, where w=weight fraction and Mw=molecular weight of the polymer. In one or more embodiments, Component B comprises at least one polymer having a critical molecular weight of entanglement ($M_c$) such that $M_c \leq wMw \leq 10^8$ g/mol, where w=weight fraction and Mw=molecular weight of the polymer.

Another aspect of the invention pertains to a A kit comprising: (a) the cosmetic composition according to any of the embodiments described above; (b) at least one container which contains the cosmetic composition according to any of the embodiments described above; and (c) at least one applicator.

Another aspect of the invention pertains to a method of applying any one of the cosmetic composition described herein to a keratinous material comprising mixing the cosmetic composition to form a mixed composition in which Component A and Component B are temporarily miscible, and applying the mixed composition to the keratinous material. In some embodiments, the keratinous material comprises a lip. In one or more embodiments, the keratinous material comprises skin.

It is to be understood that both the foregoing general description and the following detailed description are exemplary and explanatory only, and are not restrictive of the invention.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Film former" or "film forming agent" as used herein means a polymer or resin that leaves a film on the substrate to which it is applied.

"Polymer" as used herein means a compound which is made up of at least two monomers.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, hydroxyalkyl groups, and polysiloxane groups. The substituent(s) may be further substituted.

"Volatile", as used herein, means having a flash point of less than about 100° C.

"Non-volatile", as used herein, means having a flash point of greater than about 100° C.

"Anhydrous" means the compositions contain less than 1% water. Preferably, the compositions of the present invention contain less than 0.5% water, and most preferably no water.

"Transfer resistance" as used herein refers to the quality exhibited by compositions that are not readily removed by contact with another material, such as, for example, a glass, lips, skin or artificial skin, for example, when eating or drinking. Transfer resistance may be evaluated by any method known in the art for evaluating such. For example, transfer resistance of a composition may be evaluated by a "kiss" test. The "kiss" test may involve application of the composition to human keratin material such as lips followed by kissing another material, for example, a glass, lips, skin or artificial skin, against the lips after expiration of a certain amount of time following application, such as 15 minutes after application. The amount of composition transferred to the substrate may then be evaluated and compared. For example, a composition may be transfer resistant if a majority of the product is left on the wearer's lips. Further, the amount transferred may be compared with that transferred by other compositions, such as commercially available compositions. In a preferred embodiment of the present invention, little or no composition is transferred to the substrate from the lips.

"Gloss" in compositions as used herein refers to compositions having with an average gloss, measured at 60°, of greater than or equal to 35, for example 40, preferably 45, 55, 60 or 65 out of 100, including all ranges and subranges therebetween such as 35-65, 40-65, etc.

The term "average gloss" denotes the gloss as it can be measured using a gloss meter, for example by spreading a layer of the composition to be tested, between 50 μm and 500 μm in thickness, on a Leneta contrast card or BYK Opacity chart of reference Form 1A Penopac using an automatic spreader. The layer covers at least the white and/or black background of the card. The deposit is left to dry for 24 hours at a temperature of room temperature and then the gloss is measured at 60° on the white background using a Byk Gardner gloss meter of reference microTRI-GLOSS. This measurement (of between 0 and 100) is repeated at least three times, and the average gloss is the average of the at least three measurements carried out.

"Adhesion" as used herein refers to the quality exhibited by compositions that adhere to a substrate after application. Adhesion may be evaluated by any method known in the art for evaluating such. For example, samples to be tested for adhesion properties can be deposited onto a surface such as a bioskin substrate. After drying, a piece of ASTM cross hatch tape can be placed on the sample, and removed at a 180° angle. Then, it can be determined how much of the sample is adhered to the tape. For example, a rating scale such as a scale of 1-3 can be used to assess the degree of sample removal from the substrate onto the tape, in which 1 is essentially no removal, 2 is some removal, and 3 is essentially complete removal.

"Tack" as used herein refers to the quality exhibited by compositions that adhere to an object after application to a substrate. Tack may be evaluated by any method known in the art for evaluating such, such as using a texture analyzer. For example, a sample can be applied to a substrate, allowed to dry, and contacted by an object such as a ½" stainless steel ball probe, after which the force associated with removal of the object can be measured.

"Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to lips and evaluating the color of the composition after an extended period of time. For example, the color of a composition may be evaluated immediately following application to lips and these characteristics may then be re-evaluated and compared after a certain amount of time. Further, these characteristics may be evaluated with respect to other compositions, such as commercially available compositions. Alternatively or additionally, long wear properties may be evaluated by applying a sample, allowing it to dry, and then abrading the sample to determine removal/loss of sample.

The composition of the present invention may be in any form, either liquid or non-liquid (semi-solid, soft solid, solid, etc.). For example, it may be a paste, a solid, a gel, or a cream. It may be an emulsion, such as an oil-in-water or water-in-oil emulsion, a multiple emulsion, such as an oil-in-water-in-oil emulsion or a water-in-oil-in-water emulsion, or a solid, rigid or supple gel. The composition of the invention may, for example, comprise an external or continuous fatty phase. The composition can also be a molded composition or cast as a stick or a dish.

The cosmetic compositions and methods of the present invention can comprise, consist of, or consist essentially of the essential elements and limitations of the invention described herein, as well as any additional or optional ingredients, components, or limitations described herein or otherwise useful in personal care.

Compositions Capable of Forming a Multilayer Structure

In accordance with various embodiments the present invention, cosmetic compositions capable of forming a multilayer structure after application to a keratinous material are provided. Such compositions allow for benefits associated with multilayer cosmetic products without having to engage in a multi-step application process.

In accordance with one or more embodiments of the present invention, the cosmetic compositions of the present invention comprise at least two Components, hereinafter referred to as "Component A" and "Component B." In further embodiments, Component A comprises a hydrocarbon film forming agent, and Component B comprises a silicone compound. Component B, for example, may comprise a silicone gum.

Component A is the component of the compositions of the present invention which forms the layer of the multilayer structure which is closest to the keratinous material after application of the composition to the keratinous material. This layer of the multilayer structure is hereinafter referred to as "Layer A." In accordance with preferred embodiments, Component A/Layer A has an affinity for the surface of the keratinous material owing to the surface energy characteristics between the two.

Component B is the component of the compositions of the present invention which forms the layer of the multilayer structure which is farthest away from the keratinous material after application of the composition to the keratinous material. This layer of the multilayer structure is hereinafter referred to as "Layer B." In accordance with preferred embodiments, Component B/Layer B has an affinity for the air interface.

In accordance with the present invention, all weight amounts and ratios set forth herein referring to Component A and Component B refer to amounts of active material (that is, non-volatile material) in these components. Similarly, all weight amounts and ratios set forth herein referring to Layer A and Layer B refer to amounts of active material as Layer A and Layer B are present after evaporation of volatile solvent.

Prior to application to a keratinous material, Component A and Component B are immiscible in the compositions of the present invention. Preferably, immiscibility of the immiscible components results from an incompatibility between the two components when the composition is at rest, incompatibility between the two components after application to a keratinous material, or both.

Preferably, immiscibility of the immiscible components results from differences such as, for example, differences in viscosity, glass transition temperature, interfacial tension, solubility parameters, density, and/or chemical/structural incompatibility of the components, and/or differences induced by temperature and/or pressure.

For example, immiscibility of the immiscible components when the composition is at rest can result from, for example, chemical/structural incompatibility, differences in the interfacial tension between the components such as, for example, differences in the interfacial tension between the phases within mutually compatible solvent(s), differences in viscosity, differences in the glass transition temperatures of the polymers within each phase and/or differences induced by temperature and/or pressure.

For example, immiscibility of the immiscible components when the composition is being applied can result from, for example, chemical/structural incompatibility, differences in the interfacial tension between the components, differences in density of the components after solvent evaporation, and/or differences induced by temperature and/or pressure.

In one or more embodiments, immediately prior to application and/or during application to a keratinous material, the composition of the present invention is mixed or blended such that Component A and Component B are temporarily miscible upon application of the composition of the present invention to a keratinous material.

After the composition of the present invention has been applied to a keratinous material, Component A separates from Component B. As the composition dries on the keratinous material to which it has been applied, immiscible Component A and Component B form a multilayer structure comprising Layer A and Layer B, respectively, on the keratinous material such as, for example:

LAYER B
LAYER A
KERATINOUS MATERIAL

According to preferred embodiments of the present invention, after compositions of the present invention have been applied to a keratinous material, Component B results in Layer B which is level: that is, Layer B is planar such that it has refractive properties to impart shine or gloss to the composition. In accordance with these embodiments, Component B has self-leveling properties: it results in a level Layer B after application. The gloss or shine of such compositions can be enhanced, if desired, by addition of one or more shine or gloss enhancing agents having high refractive index properties. Alternatively, such compositions can be provided with matte properties by addition of one or more mattifying agents.

According to preferred embodiments of the present invention, after compositions of the present invention have been applied to a keratinous material, Component B results in Layer B which is not-level: that is, Layer B is not planar such that it imparts matte properties to the composition. In accordance with these embodiments, Component B does not have self-leveling properties: it results in a non-level Layer B after application. The matte properties of such compositions can be enhanced, if desired, by addition of one or more mattifying agents. Alternatively, such compositions can be provided with shine or gloss properties by addition of one or more shine or gloss enhancing agents having high refractive index properties.

In accordance with the present invention, the multilayer structure comprises Layer A and Layer B. In certain instances, depending on factors such as ingredient ratios, ingredient concentrations, solvent evaporation characteristics, and Tg of polymers, the layers might be intermixed slightly with each other after application to a keratinous material, resulting in Layer A having a larger amount of A and a smaller amount of B greater and/or Layer B having a larger amount of B and a smaller amount of A. Preferably, Layer A comprises 40% or less of Layer B, preferably 30% or less of Layer B, preferably 20% or less of Layer B, preferably 10% or less of Layer B, and preferably 5% or less of Layer B, including all ranges and subranges therebetween. Similarly, preferably, Layer B comprises 40% or less of Layer A, preferably 30% or less of Layer A, preferably 20% or less of Layer B, preferably 10% or less of Layer B, and preferably 5% or less of Layer A, including all ranges and subranges therebetween.

Factors affecting the separation of Component A and Component B after application to a keratinous material can include, for example, those properties discussed above including but not limited to the surface energy of the substrate, the density of each Component, the evaporation properties of the solvent(s), the Tg of the film formers, and/or the viscosity of the film formers.

Although not wishing to be bound by any particular theory, it is believed that Component A has a surface energy properties closer to the surface energy properties of the keratinous material to which it is applied than Component B. For example, the surface energy of skin is estimated to be 36 mN/m. Accordingly, where Component A has a surface energy of about 36 mN/m, it is believed that Component A can migrate to the skin. Component B would preferably have a lower surface energy, making it more likely that it would migrate toward the air interface.

Although not wishing to be bound by any particular theory, it is believed that interfacial tension of Components A and B affects phase separation (in particular, the rate at which the Components A and B separate after application). It is believed that such phase separation can be affected by differences such as those discussed above such as, for example, differences in temperature of the Components A and B, in the Tg of the Components A and B (the higher the Tg of a component, the longer it will take for phase separation), in the weight fraction of the film formers, and/or in the pressure of the Components A and B.

Such differences will also be discussed further below.

Glass Transition Temperature (Tg)

According to preferred embodiments, Component A and/or Component B comprises at least one hydrocarbon-containing film forming agent having at least one glass transition temperature lower than 60° C., preferably lower than 55° C., preferably lower than 50° C., and preferably lower than normal human body temperature (98.6° F. or 37° C.). Preferably, Component A and/or Component B comprises at least one film forming agent which has all of its glass transition temperature(s) below human body temperature (98.6° F. or 37° C.). A plasticizer can be added to adjust Tg of the film forming agent(s) as is known in the art. According to preferred embodiments, Layer A and Layer B both comprise at least one forming agent having a glass transition temperature of less than 37° C.

A preferred method of determining Tg is to remove all volatile solvent from the Layer, and determining Tg by Differential Scanning Calorimetry.

Density

According to preferred embodiments, Component A and Component B have different density properties, and the difference is such that Component A and Component B are immiscible in the compositions of the present invention. Preferably, Component A/Layer A and Component B/Layer B have a density difference of 0.001-1 kg/m$^3$, preferably 0.005-0.8 kg/m$^3$, and preferably 0.01-0.6 kg/m$^3$.

Temperature

According to preferred embodiments, Component A and Component B are affected by temperature, and the effect is such that Component A and Component B are immiscible in the compositions of the present invention at temperatures below 50° C. for a predetermined amount of time as is known in the art unlike emulsions which are considered to be stable under such conditions.

Weight Fraction

According to preferred embodiments, Component A and/or Component B comprises at least one polymer such as, for example a film forming agent having a critical molecular weight of entanglement ($M_e$) such that:

If present in Component A, the at least one polymer has an $M_c$<wMw, where w=weight fraction and Mw=molecular weight of the polymer; and If present in Component B, the at least one polymer has $M_c \leq wMw \leq 10^8$ g/mol.

Further, according to preferred embodiments, the viscosity of the at least one polymer in Component B is greater than 350 cSt, preferably greater than 500 cSt, preferably greater than 750 cSt, and preferably greater than 1000 cSt, including all ranges and subranges therebetween.

Ingredients

Component A and Component B can differ in various ways based primarily on the different functionalities associated with Layer A and Layer B. For example, where Layer A performs a transfer-resistance or adherence function, ingredients of Component A can be chosen to effect transfer-resistance or adherence. Similarly, where Layer A performs a color-enhancing function, at least one coloring agent can be added to Component A. And, for example, where Layer B performs a gloss- or shine-enhancing function and/or and provides a better feel (for example, affords a more comfortable feeling) and/or provides a barrier layer to inhibit color transfer, ingredients of Component B can be chosen to effect gloss, shine, comfort and/or barrier layer properties. However, it should be understood that at the interface of Layer A and Layer B, the interface of Layer A may possess properties more associated with Layer B (for example, shine) while Layer B may possess properties more associated with Layer A (for example, adhesion).

According to preferred embodiments, Component A comprises at least one film forming agent, at least one coloring agent, or both, and Layer A provides adhesion, transfer-resistance and/or color properties to the multilayer structure. According to such embodiments, Component B may comprise at least one shine-enhancing agent, at least one comfort agent and/or at least one barrier agent, and Layer B provides shine, comfort and/or a barrier properties to the multilayer structure.

According to preferred embodiments, the compositions of the present invention contain less than 1% wax and/or less than 1% fluorinated compound.

According to preferred embodiments, the compositions of the present invention contain less than 0.5% wax and/or less than 0.5% fluorinated compound.

According to preferred embodiments, the compositions of the present invention contain no wax and/or no fluorinated compound.

According to preferred embodiments, at least one of the same solvent(s) is used in Component A and Component B. Preferably, of total solvent present in each Component, the majority in each Component is the same.

According to preferred embodiments, the weight ratio of Component A to Component B is from 1:50 to 50:1, 1:75 to 20:1, from 1:50 to 10:1, OR from 1:20 to 10:1, including all ranges and subranges therebetween.

Examples of acceptable ingredients added to Component A and/or Component B are discussed below.

Film Forming Agent (Film Former)

Compositions of the present invention may comprise at least one hydrocarbon-containing film forming agent. As used herein, "hydrocarbon-containing film forming agent" refers to a film forming agent comprising at least about 2.5, 5, 10, 20, 30, 40, 50, 60, 70, 80, 90, 95, or 99% hydrocarbon by weight. In further embodiments, the hydrocarbon-containing film forming agent comprises less than about 5 or 1% silicone resins, and in yet further embodiments, no silicone resins.

hydrocarbon-containing film forming agents are known in the art, and any hydrocarbon-containing film forming agent may be used. According to preferred embodiments, at least one hydrocarbon-containing film forming agent having at least one glass transition temperature lower than 60° C., preferably lower than 55° C., preferably lower than 50° C., and preferably lower than normal human body temperature (98.6° F.), is included in the composition of the present invention. Preferably, the at least one hydrocarbon-containing film forming agent has all of its glass transition temperature(s) below 60° C., preferably below than 55° C., preferably below than 50° C., and preferably below than normal human body temperature (98.6° F.). The Tg property of the at least one hydrocarbon-containing film forming agent can result from various ways known in the art such as, for example, the Tg of the hydrocarbon-containing film forming agent itself, the combination of different film forming agents to achieve a Tg lower than normal human body temperature, or the combination of film forming agent(s) and plasticizer(s) to achieve a Tg lower than normal human body temperature.

Examples of acceptable classes of film forming agents include acrylic polymers, acrylate copolymers, vinyl pyrrolidone (VP) containing homopolymers and copolymers, polyurethanes, polyolefins and mixtures thereof.

Acrylic Polymers

Acceptable acrylic polymer film forming agents are known in the art and include, but are not limited to, those disclosed in U.S. patent application 2004/0170586 and U.S. patent application 2011/0020263, the entire contents of which are hereby incorporated by reference in their entirety.

"Acrylic polymer film formers" as used herein refers to polymers that are film forming agents and which are based upon one or more (meth)acrylic acid (and corresponding (meth)acrylate) monomers or similar monomers. In further embodiments, the acrylic polymer film formers do not contain a silicone or siloxane group.

Non-limiting representative examples of such film forming agents include copolymers containing at least one apolar monomer, at least one olefinically unsaturated monomer, and at least one vinylically functionalized monomer.

For the apolar monomers, acrylic monomers which comprise acrylic and methacrylic esters with alkyl groups composed of 4 to 14 C atoms, preferably 4 to 9 C atoms are preferred. Examples of monomers of this kind are n-butyl acrylate, n-butyl methacrylate, n-pentyl acrylate, n-pentyl methacrylate, n-amyl acrylate, n-hexyl acrylate, hexyl methacrylate, n-heptyl acrylate, n-octyl acrylate, n-octyl methacrylate, n-nonyl acrylate, isobutyl acrylate, isooctyl acrylate, isooctyl methacrylate, and their branched isomers, such as, for example, 2-ethylhexyl acrylate, 2-ethylhexyl methacrylate.

For olefinically unsaturated monomers, it is preferred to use monomers having functional groups selected from hydroxyl, carboxyl, sulphonic acid groups, phosphonic acid groups, acid anhydrides, epoxides, and amines. Particularly preferred examples of olefinically unsaturated monomers include acrylic acid, methacrylic acid, itaconic acid, maleic acid, fumaric acid, crotonic acid, aconitic acid, dimethylacrylic acid, beta-acryloyloxypropionic acid, trichloracrylic acid, vinylacetic acid, vinylphosphonic acid, itaconic acid, maleic anhydride, hydroxyethyl acrylate, hydroxypropyl acrylate, hydroxyethyl methacrylate, hydroxypropyl methacrylate, 6-hydroxyhexyl methacrylate, allyl alcohol, glycidyl acrylate, glycidyl methacrylate.

For vinylically functionalized compounds, preferred monomers include monomers which are copolymerizable with one or both of the previously discussed monomers and include, for example, methyl acrylate, ethyl acrylate, propyl acrylate, methyl methacrylate, ethyl methacrylate, benzyl acrylate, benzyl methacrylate, sec-butyl acrylate, tert-butyl acrylate, phenyl acrylate, phenyl methacrylate, isobornyl acrylate, isobornyl methacrylate, tert-butylphenyl acrylate, tert-butylphenyl methacrylate, dodecyl methacrylate, iso-decyl acrylate, lauryl acrylate, n-undecyl acrylate, stearyl acrylate, tridecyl acrylate, behenyl acrylate, cyclohexyl methacrylate, cyclopentyl methacrylate, phenoxyethyl acrylate, phenoxyethyl methacrylate, 2-butoxyethyl methacrylate, 2-butoxyethyl acrylate, 3,3,5-trimethylcyclohexyl acrylate, 3,5-dimethyladamantyl acrylate, 4-cumylphenyl methacrylate, cyanoethyl acrylate, cyanoethyl methacrylate, 4-biphenyl acrylate, 4-biphenyl methacrylate, 2-naphthyl acrylate, 2-naphthyl methacrylate, tetrahydrofurfuryl acrylate, diethylaminoethyl acrylate, diethylaminoethyl methacrylate, dimethylaminoethyl acrylate, dimethylaminoethyl methacrylate, 2-butoxyethyl acrylate, 2-butoxyethyl methacrylate, methyl 3-methoxyacrylate, 3-methoxybutyl acrylate, phenoxyethyl acrylate, phenoxyethyl methacrylate, 2-phenoxyethyl methacrylate, butyldiglycol methacrylate, ethylene glycol acrylate, ethylene glycol monomethylacrylate, methoxy-polyethylene glycol methacrylate 350, methoxy-polyethylene glycol methacrylate 500, propylene glycol monomethacrylate, butoxydiethylene glycol methacrylate, ethoxytriethylene glycol methacrylate, dimethylaminopropylacrylamide, dimethylaminopropylmethacrylamide, N-(1-methylundecyl)acrylamide, N-(n-butoxymethyl)acrylamide, N-(butoxymethyl)methacrylamide, N-(ethoxymethyl)acrylamide, N-(n-octadecyl)acrylamide, and also N,N-dialkyl-substituted amides, such as, for example, N,N-dimethylacrylamide, N,N-dimethylmethacrylamide, N-benzylacrylamides, N-isopropylacrylamide, N-tert-butylacrylamide, N-tert-octylacrylamide, N-methylolacrylamide, N-methylolmethacrylamide, acrylonitrile, methacrylonitrile, vinyl ethers, such as vinyl methyl ether, ethyl vinyl ether, vinyl isobutyl ether, vinyl esters, such as vinyl acetate, vinyl chloride, vinyl halides, vinylidene chloride, vinylidene halide, vinylpyridine, 4-vinylpyridine, N-vinylphthalimide, N-vinyllactam, N-vinylpyrrolidone, styrene, a- and p-methylstyrene, a-butylstyrene, 4-n-butylstyrene, 4-n-decylstyrene, 3,4-dimethoxystyrene, macromonomers such as 2-polystyrene-ethyl methacrylate (molecular weight Mw of 4000 to 13 000 g/mol), poly(methyl methacrylate)ethyl methacrylate (Mw of 2000 to 8000 g/mol).

An example of an acrylic polymer is a copolymer of acrylic acid, isobutyl acrylate and isobornyl acetate such as that sold under the names Pseudoblock (Chimex) and Synamer-3. In both of these commercial products, the copolymer is present with a solvent in a 1:1 ratio (50% solid). Another preferred film former is Poly(isobornyl methacrylate-8 co-isobornyl acrylate-co-isobutyl acrylate-co-acrylic acid) at 50% of active material in 50% of octyldodecyl neopentanoate, (Mexomere PAZ from Chimex).

Vinylpyrrolidone Polymers

Acceptable vinylpyrrolidone homopolymers or copolymers include, for example, crosslinked or non-crosslinked vinylpyrrolidone homopolymers such as the Polymer ACP- 10, as well as copolymers produced from alpha-olefin and vinylpyrrolidone in which, preferably, the copolymer contains vinylpyrrolidone and an alkyl component containing at least one C4-C30 moiety in a concentration preferably from 10 to 80 percent such as those available from Ashland under the Ganex name such as, for example, VP/eicosene (GANEX V-220) and VP/tricontanyl copolymer (GANEX WP660).

According to preferred embodiments, the film forming agent(s) is/are preferably present in an amount of from about 0.05% to about 90% by weight, preferably from 0.08% to 80% by weight, and preferably from 0.1% to 60% by weight of the total weight of the component in which they are found, including all ranges and subranges therebetween.

According to preferred embodiments, the film forming agent(s) is/are preferably present in an amount of from about 0.1% to 60% by weight, preferably from 0.2% to 55% by weight, and preferably from 0.3% to 50% by weight of the total weight of the composition, including all ranges and subranges therebetween.

High Viscosity Ester

The cosmetic composition of the present invention also contains at least one high viscosity ester. Examples thereof include, but not limited to, $C_1$-$C_{30}$ monoesters and polyesters of sugars and related materials. These esters are derived from a sugar or polyol moiety and one or more carboxylic acid moieties. Depending on the constituent acid and sugar, these esters can be in either liquid or solid form at room temperature. Suitable liquid esters include, but are not limited to: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoletate, sucrose hexaoleate, sucrose hepatoleate, sucrose octaoleate, and mixtures thereof. Suitable solid esters may include, but are not limited to: sorbitol hexaester in which the carboxylic acid ester moieties are palmitoleate and arachidate in a 1:2 molar ratio; the octaester of raffinose in which the carboxylic acid ester moieties are linoleate and behenate in a 1:3 molar ratio; the heptaester of maltose wherein the esterifying carboxylic acid moieties are sunflower seed oil fatty acids and lignocerate in a 3:4 molar ratio; the octaester of sucrose wherein the esterifying carboxylic acid moieties are oleate and behenate in a 2:6 molar ratio; and the octaester of sucrose wherein the esterifying carboxylic acid moieties are laurate, linoleate and behenate in a 1:3:4 molar ratio. In an embodiment, the ester is a sucrose polyester in which the degree of esterification is 7-8, and in which the fatty acid moieties are C18 mono- and/or di-unsaturated and behenic, in a molar ratio of unsaturates:behenic of 1:7 to 3:5. In another embodiment, the sugar polyester is the octaester of sucrose in which there are about 7 behenic fatty acid moieties and about oleic acid moiety in the molecule. Other materials may include cottonseed oil or soybean oil fatty acid esters of sucrose.

In one or more embodiments, the high viscosity ester comprises sucrose acetate isobutyrate. One example of a suitable sucrose acetate isobutyrate compound is SAIB-100®, commercially available from Eastman®, Kingsport, Tenn. This ester has a viscosity of about 100,000 cps at 30° C. and a refractive index of about 1.5 at 20° C.

Silicone Compounds

In one or more embodiments, Component B comprises one or more silicone compounds. As used herein, "silicone compound" refers to a compound comprising silicone having a surface energy lower than that of the silicone-containing film forming agents in component A. In one or more embodiments, the term refers to a compound, which may be polymeric, comprising a silicon bonded to a minimum of one oxygen, and in even further embodiments, two oxygens. In some embodiments, the silicon is bonded to a hydrocarbon (e.g., C1-22 linear, branched, and/or aryl). In further embodiments, the hydrocarbon is selected from the group consisting of methyl, ethyl, propyl, and phenyl. In one or more embodiments, the silicone compound comprises a polydimethylsiloxane (PDMS). In some embodiments, the silicone compound itself may be linear, branched or dendritic. In further embodiments, the silicone compound is linear or substantially linear. In one or more embodiments, the silicone compound comprises a chain termination selected from the group consisting of hydrocarbon, alcohol, ester, acid, ketone, amine, amide, epoxy, vinylogous (e.g. alkene or alkyne group), halogen, hydride, and the like. For example, in embodiments where the silicone compound comprises polydimethylsiloxane, the compound may be chain end terminated with an —OH or a methyl group.

In one or more embodiments, the term "silicone compound" includes, but is not limited to, silicone gums, silicone fluids, silicone wax, and the like. The silicone compounds may impart properties on the composition (e.g., enhance shine or matte quality). In one or more embodiments, the silicone compounds are present in an amount sufficient to achieve a viscosity of greater than about 1,000 cSt and/or less than about 10,000,000 cSt. In some embodiments, the viscosity ranges from about 1,000, 5,000, 10,000, 20,000, 30,000, 40,000, 50,000 or 60,000 cSt to about 100,000, 200,000, 300,000, 400,000, 500,000, 900,000, 1,000,000, 5,000,000, or 10,000,000 cSt.

Shine (Gloss) Enhancing Agents

According to preferred embodiments of the present invention, at least one shine enhancing agent can be added to Component A, Component B, or both. Preferably, the shine (gloss) enhancing agent is selected from the group consisting of agents which facilitate self-leveling of a layer, agents which have a high refractive index, or mixtures thereof.

Suitable shine enhancing agents include those compounds having a refractive index ranging from about 1.45 to about 1.60, and a weight average molecular weight of less than 15,000, preferably less than 10,000, and preferably less than 2,000. Examples of such agents include, but are not limited to, phenylated silicones such as those commercialized under the trade name "ABIL AV 8853" by Goldschmidt, those commercialized under the trade names "DC 554", "DC 555", "DC 556" and "SF 558" by Dow Corning, and those commercialized under the trade name "SILBIONE 70633 V 30" by Rhone-Poulenc.

Additional examples of suitable phenylated silicones include, but are not limited to, those commercialized by Wacker Silicones such as BELSIL PDM 20, a phenylated silicone with a viscosity at 25° C. of approximately 20 cSt; BELSIL PDM 200, a phenylated silicone with a viscosity at 25° C. of approximately 200 cSt; BELSIL PDM 1000, a phenylated silicone with a viscosity at 25° C. of approximately 1000 cSt.

Additional examples of suitable shine enhancing agents include, but are not limited to, polycyclopentadiene, poly (propylene glycol) dibenzoate (nD=1.5345), aminopropyl phenyl trimethicone (nD=1.49-1.51), pentaerythrityl tetraoleate commercially available as PURESYN 4E68 (nD=1.473) from ExxonMobil, and PPG-3 benzyl ether myristate commercially available as CRODAMOL STS (nD=1.4696) from Croda Inc.

Particularly preferred shine enhancing agents are the phenylated silicones such as phenyl trimethicone, and trimethyl pentaphenyl trisiloxane, and esters such as pentaerythrityl tetraoleate, and PPG-3 benzyl ether myristate.

Suitable shine enhancing agents include those which provide self-leveling properties to the compositions of the present invention. Suitable examples of such compositions include, but are not limited to, the silicone gums discussed below.

The silicone gum can correspond to the formula:

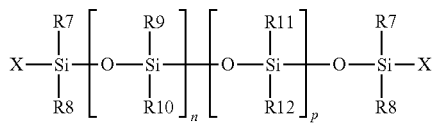

in which:

$R_7$, $R_8$, $R_{11}$ and $R_{12}$ are identical or different, and each is chosen from alkyl radicals comprising from 1 to 6 carbon atoms, $R_9$ and $R_{10}$ are identical or different, and each is chosen from alkyl radicals comprising from 1 to 6 carbon atoms and aryl radicals, X is chosen from alkyl radicals comprising from 1 to 6 carbon atoms, a hydroxyl radical and a vinyl radical, n and p are chosen so as to give the silicone gum a viscosity of from 350 cSt to 50,000,000 cSt, preferably from 500 cSt to 40,000,000 cSt, preferably from 750 cSt to 30,000,000 cSt, preferably from 850 cSt to 20,000,000 cSt, preferably from 950 cSt to 18,000,000 cSt and preferably from 1000 cSt to 10,000,000 cSt, including all ranges and subranges therebetween. A particularly preferred range is from 20,000 cSt to 800,000 cSt, with 25,000 cSt to 750,000 cSt being most preferred.

In general, n and p can each take values ranging from 0 to 10,000, such as from 0 to 5,000.

Among the silicone gums which can be used according to the invention, mention may be made of those for which:

the substituents $R_7$ to $R_{12}$ and X represent a methyl group, p=0 and n=2 700, such as the product sold or made under the name SE30 by the company General Electric, the substituents $R_7$ to $R_{12}$ and X represent a methyl group, p=0 and n=2 300, such as the product sold or made under the name AK 500 000 by the company Wacker, the substituents $R_7$ to $R_{12}$ represent a methyl group, the substituent X represents a hydroxyl group, p=0 and n=2 700, as a 13% solution in cyclopentasiloxane, such as the product sold or made under the name Q2-1401 by the company Dow Corning, the substituents $R_7$ to $R_{12}$ represent a methyl group, the substituent X represents a hydroxyl group, p=0 and n=2 700, as a 13% solution in polydimethylsiloxane, such as the product sold or made under the name Q2-1403 by the company Dow Corning, and the substituents $R_7$, $R_8$, $R_{11}$, $R_{12}$ and X represent a methyl group and the substituents $R_9$ and $R_{10}$ represent an aryl group, such that the molecular weight of the gum is about 600 000, for instance the product sold or made under the name 761 by the company Rhône-Poulenc (Rhodia Chimie).

In preferred embodiments, the silicone gum correspond to the following formula:

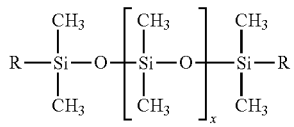

In this formula the terminal Si's can also be other than methyl and may be represented with substitutions on the repeating Si such that the R group is an alkyl of 1 to 6 carbon atoms, which may be linear, branched and/or functionalized selected from methyl, ethyl, propyl, isopropyl, butyl, isobutyl, t-butyl, amyl, hexyl, vinyl, allyl, cycohexyl, phenyl, and mixtures thereof. The silicone gums employed in the present invention may be terminated by triorganosilyl groups of the formula $R'_3$ where R' is a radical of monovalent hydrocarbons containing from 1 to 6 carbon atoms, hydroxyl groups, alkoxyl groups and mixtures thereof.

According to preferred embodiments, Component B/Layer B comprises at least one shine (gloss) enhancing agent.

According to preferred embodiments, Component B/Layer B has a self-leveling property which results in a flatter interface between Layer A and Layer B and/or between Layer B and air, and this flatter interface results in light diffraction, refraction and/or reflection properties for Layer B which enhances the shine of the composition.

According to preferred embodiments of the present invention, at least two silicone compounds such as silicone fluids (for example, phenylated silicones described above) and/or silicone gums are present in the compositions of the present invention.

According to preferred embodiments, if present, agent(s) which facilitate self-leveling of a layer such as silicone gum(s) is/are preferably present in an amount of from about 0.01% to about 90% by weight, preferably from 1% to 85% by weight, and preferably from 5% to 80% by weight of the total weight of the composition, including all ranges and subranges therebetween.

According to preferred embodiments, if present, agent(s) which have a high refractive index such as phenylated silicone oil(s) is/are preferably present in an amount of from about 0.05% to about 90% by weight, preferably from 0.1% to 75% by weight, and preferably from 1% to 50% by weight of the total weight of the composition, including all ranges and subranges therebetween.

According to preferred embodiments of the present invention, at least two silicone compounds such as silicone fluids (for example, phenylated silicones described above) and/or silicone gums are present in the compositions of the present invention.

According to preferred embodiments, the shine enhancing (s) is/are preferably present in an amount of from about 0.05% to about 90% by weight, preferably from 0.1% to 50% by weight, and preferably from 1% to 35% by weight of the total weight of the composition, including all ranges and subranges therebetween.

Matte Enhancing Agents (Mattifying Agent)

According to preferred embodiments of the present invention, at least one matte enhancing agent can be added to Component A, Component B, or both. With respect to Component B, the at least one matte enhancing agent can be added regardless of whether Component B is not self-leveling and/or Layer B has refractive properties to impart matte properties to the composition as described above.

Suitable matte enhancing agents include, but are not limited to, mattifying fillers such as, for example, talc, silica, silicone elastomers, and polyamides, and waxes such as, for example, beeswax and copernicia cerifera (carnauba) wax.

According to preferred embodiments, the matte enhancing (s) is/are preferably present in an amount of from about 0.05% to about 90% by weight, preferably from 0.1% to 50% by weight, and preferably from 1% to 35% by weight of the total weight of the composition, including all ranges and subranges therebetween.

Coloring Agents

According to preferred embodiments of the present invention, compositions further comprising at least one coloring agent are provided. Preferably, such colored compositions can be cosmetic compositions such as, for example, lip compositions (for example, lipstick) or foundations.

According to this embodiment, the at least one coloring agent is preferably chosen from pigments, dyes, such as liposoluble dyes, nacreous pigments, and pearling agents.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, annatto, and quinoline yellow. The liposoluble dyes, when present, generally have a concentration ranging up to 20% by weight of the total weight of the composition, such as from 0.0001% to 6%, including all ranges and subranges therebetween.

The nacreous pigments which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, be present in the composition in a concentration ranging up to 50% by weight of the total weight of the composition, such as from 0.1% to 20%, preferably from 0.1% to 15%, including all ranges and subranges therebetween.

The pigments, which may be used according to the present invention, may be chosen from white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, strontium, calcium, and aluminum.

If present, the coloring agents may be present in the composition in a concentration ranging up to 50% by weight of the total weight of the composition, such as from 0.01% to 40%, and further such as from 0.1% to 30%, including all ranges and subranges therebetween. In the case of certain products, the pigments, including nacreous pigments, may, for example, represent up to 50% by weight of the composition.

Oil Phase

According to preferred embodiments of the present invention, compositions further comprising at least one fatty substance are provided. Suitable fatty substances include oil(s) and/or wax(es). "Oil" means any non-aqueous medium which is liquid at ambient temperature (25° C.) and atmospheric pressure (760 mm Hg). A "wax" for the purposes of the present disclosure is a lipophilic fatty compound that is solid at ambient temperature (25° C.) and changes from the solid to the liquid state reversibly, having a melting temperature of more than 30° C. and, for example, more than 45° C., which can be as high as 150° C., a hardness of more than 0.5 MPa at ambient temperature, and an anisotropic crystalline organization in the solid state. By taking the wax to its melting temperature, it is possible to use wax(es) by themselves as carriers and/or it is possible to make wax(es) miscible with the oils to form a microscopically homogeneous mixture.

Suitable oils include volatile and/or non-volatile oils. Such oils can be any acceptable oil including but not limited to silicone oils and/or hydrocarbon oils.

According to certain embodiments, the compositions of the present invention preferably comprise one or more volatile silicone oils. Examples of such volatile silicone oils include linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
|---|---|---|
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane (L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |

Further, a volatile linear silicone oil may be employed in the present invention. Suitable volatile linear silicone oils include those described in U.S. Pat. No. 6,338,839 and WO03/042221, the contents of which are incorporated herein by reference. In one embodiment the volatile linear silicone oil is decamethyltetrasiloxane. In another embodiment, the decamethyltetrasiloxane is further combined with another solvent that is more volatile than decamethyltetrasiloxane.

According to certain embodiments of the present invention, the composition of preferably comprises one or more non-silicone volatile oils and may be selected from volatile hydrocarbon oils, volatile esters and volatile ethers. Examples of such volatile non-silicone oils include, but are not limited to, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isohexacecane, isododecane, isodecane, and for example, the oils sold under the trade names of Isopar or Permethyl. Preferably, the volatile non-silicone oils have a flash point of at least 40° C.

Non-limiting examples of volatile non-silicone volatile oils are given in Table 2 below.

TABLE 2

| Compound | Flash Point (° C.) |
|---|---|
| Isododecane | 43 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

The volatility of the solvents/oils can be determined using the evaporation speed as set forth in U.S. Pat. No. 6,338,839, the contents of which are incorporated by reference herein.

According to certain embodiments of the present invention, the composition comprises at least one non-volatile oil. Examples of non-volatile oils that may be used in the present invention include, but are not limited to, polar oils such as:

hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;

synthetic oils or esters of formula $R_5COOR_6$ in which $R_5$ represents a linear or branched higher fatty acid residue containing from 1 to 40 carbon atoms, including from 7 to 19 carbon atoms, and $R_6$ represents a branched hydrocarbon-based chain containing from 1 to 40 carbon atoms, including from 3 to 20 carbon atoms, with $R_6+R_7 \geq 10$, such as, for example, Purcellin oil (cetostearyl octanoate), isononyl isononanoate, octyldodecyl neopentanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

synthetic ethers containing from 10 to 40 carbon atoms;

$C_8$ to $C_{26}$ fatty alcohols, for instance oleyl alcohol, cetyl alcohol, stearyl alcohol, and cetearly alcohol; and mixtures thereof.

Further, examples of non-volatile oils that may be used in the present invention include, but are not limited to, non-polar oils such as branched and unbranched hydrocarbons and hydrocarbon waxes including polyolefins, in particular Vaseline (petrolatum), paraffin oil, squalane, squalene, hydrogenated polyisobutene, hydrogenated polydecene, polybutene, mineral oil, pentahydrosqualene, and mixtures thereof.

According to preferred embodiments, if present, the at least one oil is present in the compositions of the present invention in an amount ranging from about 5 to about 60% by weight, more preferably from about 10 to about 50% by weight, and most preferably from about 15 to about 35% by weight, based on the total weight of the composition, including all ranges and subranges within these ranges.

According to preferred embodiments of the present invention, the compositions of the present invention further comprise at least one wax. Suitable examples of waxes that can be used in accordance with the present disclosure include those generally used in the cosmetics field: they include those of natural origin, such as beeswax, carnauba wax, candelilla wax, ouricoury wax, Japan wax, cork fibre wax or sugar cane wax, rice wax, montan wax, paraffin wax, lignite wax or microcrystalline wax, ceresin or ozokerite, and hydrogenated oils such as hydrogenated castor oil or jojoba oil; synthetic waxes such as the polyethylene waxes obtained from the polymerization or copolymerization of ethylene, and Fischer-Tropsch waxes, or else esters of fatty acids, such as octacosanyl stearate, glycerides which are concrete at 30° C., for example at 45° C.

According to particularly preferred embodiments of the present invention, the compositions of the present invention further include at least one silicone wax. Examples of suitable silicone waxes include, but are not limited to, silicone waxes such as alkyl- or alkoxydimethicones having an alkyl or alkoxy chain ranging from 10 to 45 carbon atoms, poly(di)methylsiloxane esters which are solid at 30° C. and whose ester chain comprising at least 10 carbon atoms, di(1,1,1-trimethylolpropane) tetrastearate, which is sold or manufactured by Heterene under the name HEST 2T-4S; alkylated silicone acrylate copolymer waxes comprising at least 40 mole % of siloxy units having the formula $(R_2R'SiO_{1/2})_x(R''SiO_{3/2})_y$, where x and y have a value of 0.05 to 0.95, R is an alkyl group having from 1 to 8 carbon atoms, an aryl group, a carbinol group, or an amino group, R is a monovalent hydrocarbon having 9-40 carbon atoms, R" is a monovalent hydrocarbon group having 1 to 8 carbon atoms, an aryl group such as those disclosed in U.S. patent application 2007/0149703, the entire contents of which is hereby incorporated by reference, with a particular example being C30-C45 alkyldimethylsilyl polypropylsilsesquioxane; and mixtures thereof.

According to preferred embodiments of the present invention, the compositions of the present invention further include at least one long-chain alcohol wax. Preferably, the at least one long-chain alcohol wax has an average carbon chain length of between about 20 and about 60 carbon atoms, most preferably between about 30 and about 50 carbon atoms. Suitable examples of long-chain alcohol waxes include but are not limited to alcohol waxes commercially available from Baker Hughes under the Performacol trade name such as, for example, Performacol 350, 425 and 550. Most preferably, the long-chain alcohol wax has a melting temperature range from about 93° C. to about 105° C.

According to preferred embodiments, the compositions of the present invention contain less than 1% wax.

According to preferred embodiments, the compositions of the present invention contain less than 0.5% wax.

According to preferred embodiments, the compositions of the present invention contain no wax.

If present, the wax or waxes may be present in an amount ranging from 1 to 30% by weight relative to the total weight of the composition, for example from 2 to 20%, and for example from 3 to 10%, including all ranges and subranges therebetween.

Aqueous Phase

The compositions of the present invention may also contain water. When the compositions of the present invention contain water, they are preferably in the form of an emulsion. Preferably, when the compositions of the present invention contain water, they are in the form of an oil-in-water emulsion (O/W) or a water-in-oil emulsion (W/O). When present, water is preferably present in an amount of from about 10% to about 80% by weight, preferably from about 20% to about 70% by weight, preferably from about 35% to about 65% by weight, including all ranges and subranges therebetween, all weights being based on the total weight of the composition.

Additional Additives

The composition of the invention can also comprise any additive usually used in the field under consideration. For example, dispersants such as poly(12-hydroxystearic acid), antioxidants, essential oils, sunscreens, preserving agents, fragrances, fillers, neutralizing agents, cosmetic and dermatological active agents such as, for example, emollients, moisturizers, vitamins, essential fatty acids, surfactants, silicone elastomers, thickening agents, gelling agents, particles, pasty compounds, viscosity increasing agents can be added. A non-exhaustive listing of such ingredients can be found in U.S. patent application publication no. 2004/0170586, the entire contents of which is hereby incorporated by reference. Further examples of suitable additional components can be found in the other references which have been incorporated by reference in this application. Still further examples of such additional ingredients may be found in the *International Cosmetic Ingredient Dictionary and Handbook* ($9^{th}$ ed. 2002).

A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture.

These additives may be present in the composition in a proportion from 0% to 99% (such as from 0.01% to 90%) relative to the total weight of the composition and further such as from 0.1% to 50% (if present), including all ranges and subranges therebetween.

In one or more embodiments, the composition of the invention is cosmetically or dermatologically acceptable, i.e., it should contain a non-toxic physiologically acceptable medium and should be able to be applied to the eyelashes of human beings.

In particular, suitable gelling agents for the oil phase include, but are not limited to, lipophilic or hydrophilic clays.

The term "hydrophilic clay" means a clay that is capable of swelling in water; this clay swells in water and forms after hydration a colloidal dispersion. These clays are products that are already well known per se, which are described, for example, in the book "Mineralogie des argiles", S. Caillere, S. Henin, M. Rautureau, $2^{nd}$ edition 1982, Masson, the teaching of which is included herein by way of reference. Clays are silicates containing a cation that may be chosen from calcium, magnesium, aluminum, sodium, potassium and lithium cations, and mixtures thereof. Examples of such products that may be mentioned include clays of the smectite family such as montmorillonites, hectorites, bentonites, beidellites and saponites, and also of the family of vermiculites, stevensite and chlorites. These clays may be of natural or synthetic origin.

Hydrophilic clays that may be mentioned include smectite products such as saponites, hectorites, montmorillonites, bentonites and beidellite. Hydrophilic clays that may be mentioned include synthetic hectorites (also known as laponites), for instance the products sold by the company Laporte under the names Laponite XLG, Laponite RD and Laponite RDS (these products are sodium magnesium silicates and in particular sodium lithium magnesium silicates); bentonites, for instance the product sold under the name Bentone HC by the company Rheox; magnesium aluminum silicates, especially hydrated, for instance the products sold by the Vanderbilt Company under the names Veegum Ultra, Veegum HS and Veegum DGT, or calcium silicates, and especially the product in synthetic form sold by the company under the name Micro-cel C.

The term "lipophilic clay" means a clay that is capable of swelling in a lipophilic medium; this clay swells in the medium and thus forms a colloidal dispersion. Examples of lipophilic clays that may be mentioned include modified clays such as modified magnesium silicate (Bentone Gel VS38 from Rheox), and hectorites modified with a $C_{10}$ to $C_{22}$ fatty-acid ammonium chloride, for instance hectorite modified with distearyldimethylammonium chloride (CTFA name: disteardimonium hectorite) sold under the name Bentone 38 CE by the company Rheox or Bentone 38V® by the company Elementis.

In particular, among the gelling agents that may be used, mention may be made of silica particles. Preferably, the silica particles are fumed silica particles.

Suitable silicas include, but are not limited to, hydrophobic silicas, such as pyrogenic silica optionally with hydrophobic surface treatment whose particle size is less than 1 micron, preferably less than 500 nm, preferably less than 100 nm, preferably from 5 nm to 30 nm, including all ranges and subranges therebetween. It is in fact possible to modify the surface of silica chemically, by a chemical reaction producing a decrease in the number of silanol groups present on the surface of the silica. The silanol groups can notably be replaced with hydrophobic groups: a hydrophobic silica is then obtained. The hydrophobic groups can be:

trimethylsiloxyl groups, which are notably obtained by treatment of pyrogenic silica in the presence of hexamethyldisilazane. Silicas treated in this way are called "Silica silylate" according to the CTFA (6th edition, 1995). They are for example marketed under the references "AEROSIL R812®" by the company Degussa, "CAB-O-SIL TS-530®" by the company Cabot;

dimethylsilyloxyl or polydimethylsiloxane groups, which are notably obtained by treatment of pyrogenic silica in the presence of polydimethylsiloxane or dimethyldichlorosilane. Silicas treated in this way are called "Silica dimethyl silylate" according to the CTFA (6th edition, 1995). They are for example marketed under the references "AEROSIL R972®", "AEROSIL R974®" by the company Degussa, "CAB-O-SIL TS-610®", "CAB-O-SIL TS-720®" by the company Cabot.

Preferably, the gelling agent, if present, is present in the nail composition of the present invention in amounts of active material generally ranging from about 0.1% to about 10%, preferably from about 0.25% to about 5%, and more preferably from about 0.5% to about 3.5%, by weight, based on the total weight of the cosmetic composition, including all ranges and subranges in between.

In particular, suitable emollients may include, but are not limited to, the following: natural and synthetic oils such as mineral, plant and animal oils; fats and waxes; fatty alcohols and acids, and their esters; esters and ethers of (poly) alkylene glycols; hydrocarbons such as petrolatum and squalane; lanolin alcohol and its derivatives; animal and plant triglycerides; and stearyl alcohol.

Non-limiting examples include, without limitation, esters such as isopropyl palmitate, isopropyl myristate, isononyl isonanoate (such as WICKENOL 151 available from Alzo Inc. of Sayreville, N.J.), C12-C15 alkyl benzoates (such as FINSOLV TN from Innospec Active Chemicals), caprylic/capric triglycerides, pentaerythritol tetraoctanoate, mineral oil, dipropylene glycol dibenzoate, PPG-15 stearyl ether benzoate, PPG-2-Myristyl Ether Propionate, ethyl methicone, diethylhexylcyclohexane, hydrocarbon-based oils of plant origin, such as liquid triglycerides of fatty acids containing from 4 to 10 carbon atoms, for instance heptanoic or octanoic acid triglycerides, sunflower oil, corn oil, soybean oil, marrow oil, grapeseed oil, sesame seed oil, hazelnut oil, apricot oil, macadamia oil, arara oil, coriander oil, castor oil, avocado oil, jojoba oil, shea butter oil, caprylyl glycol; synthetic esters and ethers, especially of fatty acids, for instance, Purcellin oil, 2-octyldodecyl stearate, 2-octyldodecyl erucate, isostearyl isostearate, hydroxylated esters, for instance isostearyl lactate, octyl hydroxystearate, octyldodecyl hydroxystearate, diisostearyl malate or triisocetyl citrate, fatty alcohol heptanoates, octanoates or decanoates, polyol esters, for instance propylene glycol dioctanoate, neopentyl glycol diheptanoate and diethylene glycol diisononanoate, pentaerythritol esters, for instance pentaerythrityl tetraisostearate, isopropyl lauroyl sarcosinate, petroleum jelly, polydecenes, hydrogenated polyisobutene such as Parleam oil, and/or the mixture of n-undecane and of n-tridecane sold under the reference Cetiol UT by the company BASF.

Preferably, the emollient agent(s), if present, is present in the composition of the present invention in amounts of active material generally ranging from about 0.1% to about 20%, preferably from about 0.25% to about 15%, and more preferably from about 0.5% to about 10%, by weight, based on the total weight of the composition, including all ranges and subranges in between.

According to preferred embodiments, the compositions of the present invention are lip compositions for application to lips such as lipsticks, lip gloss or lip balms. In accordance with these embodiments, the compositions of the present invention can contain ingredients typically found in lip compositions such as, for example, coloring agents, waxes, and gelling agents. Further, the compositions can contain water or be anhydrous. Also, the compositions can be solid or non-solid.

According to preferred embodiments, the compositions of the present invention are skin compositions for application to skin such as foundations, moisturizers, sunscreens, blush, eyeshadows, etc. In accordance with these embodiments, the compositions of the present invention can contain ingredients typically found in skin compositions such as, for example, coloring agents, active ingredients, humectants, surfactants and fillers. Further, the compositions can contain water or be anhydrous. Also, the compositions can be solid or non-solid.

According to preferred embodiments, the compositions of the present invention are hair compositions for application to hair such as shampoos, conditioners, styling mousses and dyes. In accordance with these embodiments, the compositions of the present invention can contain ingredients typically found in hair compositions such as, for example, coloring agents, surfactants, moisturizers, and active agents. Further, the compositions can contain water or be anhydrous. Also, the compositions can be in various forms such as liquid, foam, and paste.

According to preferred embodiments, the compositions of the present invention are nail compositions for application to nails such as primer compositions, color compositions or topcoat compositions. In accordance with these embodiments, the compositions of the present invention can contain ingredients typically found in nail compositions such as, for example, coloring agents, polymerizable compounds, and solvents. Further, the compositions can contain water or be anhydrous.

According to preferred embodiments, the compositions of the present invention are eyelash compositions for application to eyelashes such as primers, mascaras and topcoats. In accordance with these embodiments, the compositions of the present invention can contain ingredients typically found in eyelash compositions such as, for example, coloring agents, waxes, and gelling agents. Further, the compositions can contain water or be anhydrous. Also, the compositions can be of any form typical for such compositions such as, for example, emulsion or dispersion.

According to preferred embodiments of the present invention, methods of treating, caring for and/or making up keratinous material such as skin, nails, eyelashes, hair and lips by applying compositions of the present invention to the keratinous material in an amount sufficient to treat, care for and/or make up the keratinous material are provided. Preferably, "making up" the keratin material includes applying at least one coloring agent to the keratin material in an amount sufficient to provide color to the keratin material.

According to yet other preferred embodiments, methods of enhancing the appearance of keratinous material by applying compositions of the present invention to the keratinous material in an amount sufficient to enhance the appearance of the keratinous material are provided.

According to preferred embodiments of the present invention, methods of applying compositions of the present invention to a keratinous material (for example, skin, nails, eyelashes, hair or lips) comprising mixing or blending the composition so that the immiscible components are temporarily miscible, and applying the composition comprising the temporarily miscible components to the keratinous material are provided. Subsequent to application to the keratinous material, the components separate to form a multilayer structure on the keratinous material.

According to preferred embodiments of the present invention, kits comprising (1) at least one container; (2) at least one applicator; and (3) at least one cosmetic composition capable of forming a multilayer structure after application to a keratinous material, wherein the composition comprises at least two immiscible components prior to application.

In accordance with the preceding preferred embodiments, the compositions of the present invention are applied topically to the desired area of the keratin material in an amount sufficient to treat, care for and/or make up the keratinous material, to cover or hide defects associated with keratinous material, skin imperfections or discolorations, or to enhance the appearance of keratinous material. The compositions may be applied to the desired area as needed, preferably once daily, and then preferably allowed to dry before subjecting to contact such as with clothing or other objects. Preferably, the composition is allowed to dry for about 4 minutes or less, more preferably for about 2 minutes or less.

Also in accordance with the preceding preferred embodiments, compositions are preferably contained in a suitable container for cosmetic compositions. Suitable shapes of such containers include, but are not limited to, any geometric shape such as, for example, square, rectangular, pyramidal, oval, circular, hemispherical, etc. Further, the container may be made of flexible or inflexible material.

Similarly, any applicator suitable for application of cosmetic compositions can be used in accordance with the present invention, with suitable examples of types of applicators including, but not limited to, a brush, stick, pad, roller ball, etc.

Preferably, either (1) the container is capable of mixing or blending the composition of the present invention so that the immiscible components are temporarily miscible; (2) the applicator is capable of mixing or blending the composition of the present invention so that the immiscible components are temporarily miscible; or (3) the container and the applicator working together are capable of mixing or blending the composition of the present invention so that the immiscible components are temporarily miscible in accordance with the preceding preferred embodiments. For example, a flexible container by virtue of its flexibility could create sufficient forces when manipulated to temporarily mix or blend the composition of the present invention so that the immiscible components are temporarily miscible; an applicator by virtue of its design could create sufficient forces when withdrawn from the container to temporarily mix or blend the composition of the present invention so that the immiscible components are temporarily miscible; or (3) an inflexible container and an applicator by virtue of their synergistic design elements could create sufficient forces when the applicator is withdrawn from the container to temporarily mix or blend the composition of the present invention so that the immiscible components are temporarily miscible.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

Example 1

Sample Preparation:

Compositions were prepared using a high speed mixer. To a high speed mixer cup, all polymers were added. The sample was mixed at 2500-3500 RPM until homogenous. The samples typically were opaque and not clear, and homogeneity was deciphered by the sample smoothness. To the freshly mixed sample, pigments, pigments dispersions, and any other particles were added in addition to the QS solvent. The sample was additionally mixed at 2500-3500 RPM until homogenous.

Film Disruption and Recovery:

Samples were evaluated for their dried film properties. Samples were casted onto a BYK Opacity Chart (#2812) using a 3 mil wet drawdown bar at room temperature. Samples were allowed to dry for a minimum of 5 hours. After drying, samples were visually and manually evaluated for phase separation and self-leveling properties. In order to assess the phase separation, films were agitated with a gloved finger. If samples could be roughened it was documented and they were further assessed for recovery of the film by self-leveling. Samples were allowed to rest for a minimum of a 24 hour period and then visually reassessed for interface quality and if there was any level of recovery. Images were also captured of the samples prior to roughening, at initial roughening, and at 24 hours after roughening. After the 24 hour period, it was documented if the sample showed signs of recovery or not.

Water Contact Angle:

To a BYK Opacity Chart (#2812) a 3 mil wet drawdown bar was used to cast a film. Films were allowed to dry for at least 48 hours prior to measurements. All contact angle measurements were captured using a tensiometer. A 2-3 microliter sessile drop was placed onto the casted films, and mean contact angle values were captured after ten seconds. For each sample a minimum of three contact angle values were taken, and an average is depicted on the table below.

The compositions in the below table were prepared and tested according to protocols set forth above. As can be seen, Inventive example 1 exhibited self-leveling properties after agitation. Moreover the water contact angle of Inventive example 1 was similar to that of Comparative example 3.

|  | Inventive 1 | Comparative 2 | Comparative 3 |
|---|---|---|---|
| Sucrose Acetate Isobutyrate (SAIB) | 10 | 10 | 0 |
| Dimethicone[1] | 10 | 0 | 10 |
| Dimethiconol[2] | 5 | 0 | 5 |
| Pigment | 3 | 3 | 3 |
| isododecane | 72 | 87 | 82 |
| Total | 100 | 100 | 100 |
| Roughened? | Yes | No | Yes |
| Recovered? | Yes | No | No |
| Water Contact Angle Average at 10 seconds | 122.014 | 102.0675 | 129.068 |

[1] XIAMETER PMX-200 SILICONE FLUID 1000CS
[2] Dow Corning 1515 Si Gum

What is claimed is:

1. A kit comprising:
   (a) a cosmetic composition comprising at least two immiscible Components A and B, wherein:
   Component A comprises about 0.01% to 60% by weight with respect to the total weight of the composition of at least one hydrocarbon-containing film forming agent having at least one glass transition temperature which is lower than 98.6° F., and
   Component B comprises about 0.01% to 90% by weight with respect to the total weight of the composition of one or more silicone compounds in amounts sufficient to achieve a viscosity of the silicone compound(s) of about 1,000 cSt to 10,000,000 cSt,
   wherein the weight ratio of hydrocarbon-containing film forming agent(s) in Component A to silicone compound(s) in Component B is from about 1:50 to 50:1;
   (b) at least one container which contains the cosmetic composition; and (c) at least one applicator, wherein the container and/or applicator is capable of mixing the cosmetic composition to form a mixed composition in which Component A and Component B are temporarily not immiscible, wherein the cosmetic composition is not in the form of an emulsion and does not contain fluorinated compound.

2. The kit of claim 1, wherein Component A comprises at least one silicone-containing film forming agent having at least one glass transition temperature lower than 60° C.

3. The kit of claim 1, wherein the cosmetic composition comprises at least one coloring agent.

4. The kit of claim 1, wherein Component B comprises at least polymer having at least one glass transition temperature lower than 60° C.

5. The kit of claim 1, wherein Component B is self-leveling such that it imparts shine to the cosmetic composition after application to a keratinous material.

6. The kit of claim 1, wherein the silicone compound comprises at least one silicone gum.

7. The kit of claim 1, wherein the silicone compound comprises at least one silicone fluid.

8. The kit of claim 1, wherein Component A and Component B have a density difference of 0.001-1 kg/m3.

9. The kit of claim 1, wherein Component A and Component B have a density difference of 0.01-0.6 kg/m3.

10. The kit of claim 1, wherein Component B comprises at least one polymer having a viscosity of about 1000 cSt to about 1,000,000 cSt.

11. The kit of claim 1, wherein the silicone compound comprises at least one polymer selected from the group consisting of a silicone gum, a silicone fluid, and mixtures thereof.

12. The kit of claim 1, wherein Component A comprises at least one polymer having a critical molecular weight of entanglement (Mc) such that $Mc<wMw$, where w=weight fraction and Mw=molecular weight of the polymer.

13. The kit of claim 1, wherein Component B comprises at least one polymer having a critical molecular weight of entanglement (Mc) such that $Mc \leq wMw \leq 108$ g/mol, where w=weight fraction and Mw=molecular weight of the polymer.

14. The kit of claim 1, wherein the at least one hydrocarbon-containing film forming agent is sucrose acetate isobutyrate.

* * * * *